(12) United States Patent
Yang et al.

(10) Patent No.: US 9,072,312 B2
(45) Date of Patent: Jul. 7, 2015

(54) BIDENS PILOSA AND POLYACETYLENIC COMPOUNDS FOR PREVENTION AND TREATMENT OF COCCIDIOSIS

(71) Applicant: ACADEMIA SINICA, Taipei (TW)

(72) Inventors: Wen-Chin Yang, Taichung County (TW); Lee-Tian Chang, Taichung (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 14/354,995

(22) PCT Filed: Oct. 27, 2012

(86) PCT No.: PCT/US2012/062322
§ 371 (c)(1),
(2) Date: Apr. 29, 2014

(87) PCT Pub. No.: WO2013/074273
PCT Pub. Date: May 23, 2013

(65) Prior Publication Data
US 2014/0308378 A1    Oct. 16, 2014

(30) Foreign Application Priority Data
Nov. 14, 2011   (TW) .............................. 100141367 A

(51) Int. Cl.
| A01N 65/00 | (2009.01) |
| A23K 1/17 | (2006.01) |
| A61K 36/00 | (2006.01) |
| A61K 36/28 | (2006.01) |
| A23K 1/14 | (2006.01) |
| A23K 1/16 | (2006.01) |
| A23K 1/18 | (2006.01) |
| A61K 31/7028 | (2006.01) |

(52) U.S. Cl.
CPC . *A23K 1/17* (2013.01); *A61K 36/00* (2013.01); *A61K 36/28* (2013.01); *A23K 1/14* (2013.01); *A23K 1/1643* (2013.01); *A23K 1/1646* (2013.01); *A23K 1/182* (2013.01); *A23K 1/1826* (2013.01); *A23K 1/188* (2013.01); *A23V 2200/32* (2013.01); *A61K 31/7028* (2013.01)

(58) Field of Classification Search
CPC ....................................................... A61K 36/00
USPC ........................................................... 424/725
See application file for complete search history.

(56) References Cited

U.S. PATENT DOCUMENTS

2010/0204166 A1    8/2010  Yang

OTHER PUBLICATIONS

Brandão MG et al. "Antimalarial activity of extracts and fractions from *Bidens pilosa* and other *Bidens* species (Asteraceae) correlated with the presence of acetylene and flavonoid compounds" J Ethnopharmacol. Jul. 1997,57 (2):131-8.

Michels MG et al. "Anticoccidial effects of coumestans from *Eclipta alba* for sustainable control of *Eimeria tenella* parasifosis in poultry production" Vet Parasitol Apr. 19, 2011;177(1-2):55-60.

*Primary Examiner* — Michael Meller
(74) *Attorney, Agent, or Firm* — Hsiu-Ming Saunders; Intellectual Property Connections, Inc.

(57) ABSTRACT

A composition for use in prevention, inhibition and/or treatment of coccidiosis in an animal is disclosed. The composition comprises an effective amount of *Bidens pilosa*, an active constituent thereof, or an active compound isolated therefrom. In another aspect, a composition for use in preventing and/or treating coccidiosis, and/or enhancing growth in an animal is disclosed, the composition comprising an animal feed and an effective amount of *Bidens pilosa*, or an isolated active constituent comprising a polyacetylenic compound.

8 Claims, 6 Drawing Sheets

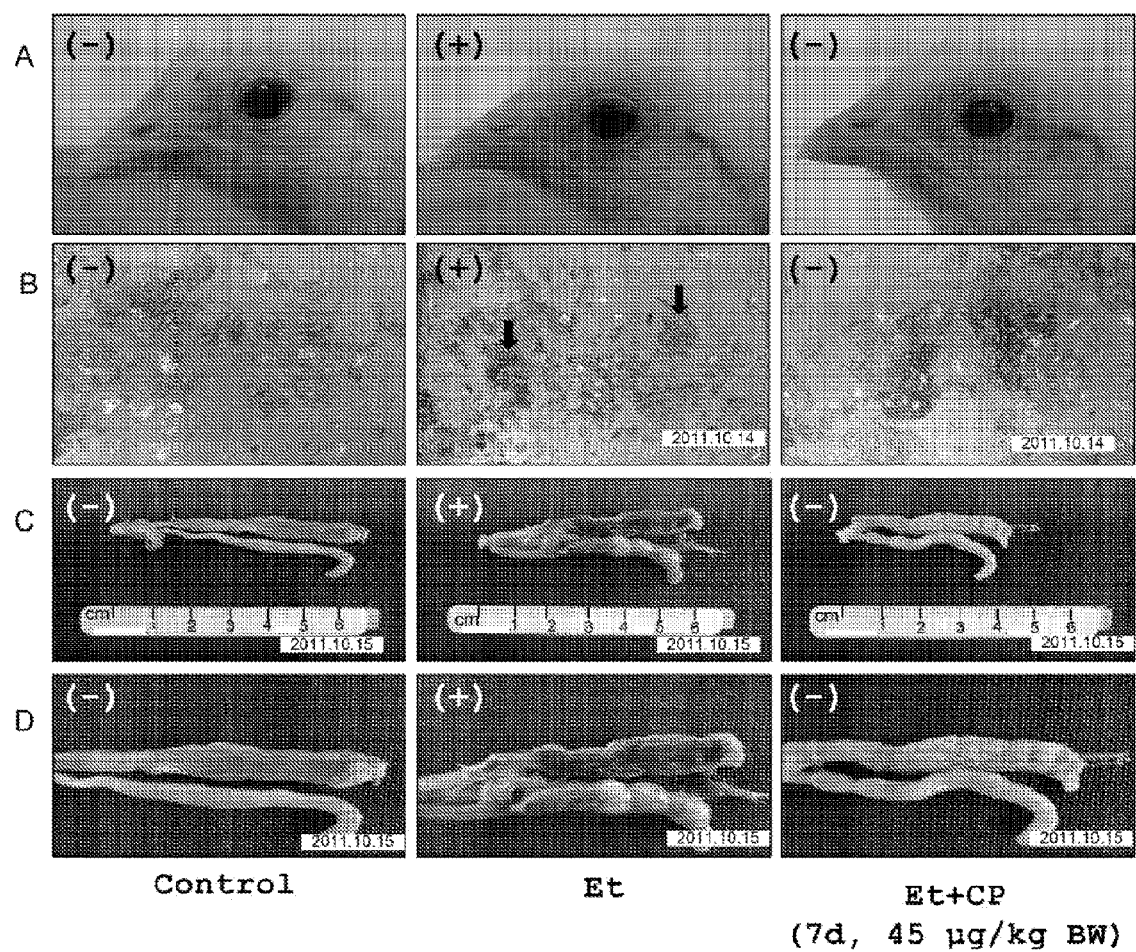

Control        Et        Et + CP

BIDENS PILOSA AND POLYACETYLENIC COMPOUNDS FOR PREVENTION AND TREATMENT OF COCCIDIOSIS

REFERENCE TO RELATED APPLICATION

This application is a national stage application (under 35 U.S.C. 371) of PCT/US2012/062322 filed on 27 Oct. 2012, which claims priority to a TW application No. 100141367 filed on 14 Nov. 2011, all of which are herein incorporated by reference in their entireties.

FIELD OF THE INVENTION

The present invention relates generally to prevention, inhibition and treatment of coccidiosis, and more specifically to plants and phytochemicals for anti-coccidiosis

BACKGROUND OF THE INVENTION

Coccidiosis may be a major parasitic disease of poultry and causes a considerable economic loss in the poultry industry. The loss due to coccidiosis includes mortality, malabsorption, inefficient feed utilization, and impaired growth rate in broilers and a temporary reduction of em production in layers. It was estimated that coccidiosis in the poultry industry in Great Britain caused a yearly loss of 61 million USD. By extrapolation, the global costs could be expected to be 2400 million USD per annum.

The genus *Eimeria*, a Coccidia subclass, belongs to spore-forming, unicellular, and obligate protozoa. That is to say, they must live and reproduce within animal cells. *Eimeria* is an intestinal parasite and can infect fishes, reptiles, birds, mammals. Of note, chickens are susceptible to at least 11 species of *Eimeria, E. tenella, E. necatrix, E. brunetti* and *E. maxima* are the more virulent species and *E. acervulina, E. praecox* and *E. mitis* are less virulent species in chickens. *Eimeria* infection is usually asymptomatic and however, shows severe clinical symptoms such as diarrhea, bloody droppings, dehydration, droopiness, listlessness, loss of appetite, paleness, ruffled feathers and huddling in young and immune-compromised animals.

The life cycle of *Eimeria* comprises intracellular, extracellular, asexual, and sexual stages. Once the chickens are infected with *Eimeria*, the parasites develop in the chicken and give rise to a microscopic egg (called an oocyst) which is passed out in the droppings. Under proper conditions of temperature and moisture the oocyst develops within one to two days to form a sporulated oocyst which is capable of infecting other chickens. At this stage the oocyst contains eight bodies (called sporozoites), each of which is capable of entering a cell in the chicken's intestine after the oocyst is eaten. When sporozoites enter the cells, they divide many times producing either a few or many offspring (merozoites). The numbers produced depend on the species of coccidia involved. Each merozoite in turn may enter another intestinal cell. This cycle may be repeated several times. Because of this cyclic multiplication, large numbers of intestinal cells are destroyed. Eventually, the cycle stops and sex cells (microgametocyte and macrogametocyte) are produced. Microgametocyte fertilizes macrogametocyte to produce and oocyst which ruptures from the intestinal cell and passes in the droppings. Thousands of oocysts may be passed in the droppings of an infected chicken. Therefore, poultry raised in crowded or unsanitary conditions are at great risk of becoming infected.

Vaccination and chemotherapeutic approach are currently used to prevent and treat coccidiosis. Live attenuated vaccines are used to prevent coccidial infection. Its advantage is lack of residual antibiotics in the chicken meat. However, the cross-species protection in coccidian vaccines is unsatisfactory. On the contrary, the most widely used compounds are the ionophore antibiotics, monensin, narasin, salinomycin, maduramicin, semduramicin and lasalocid, which prevent the development of first generation schizonts of the *Eimeria* genus. However, antibiotic-resistant *Eimeria* strains have recently been isolated. Moreover, the residual antibiotics in chicken meat have been a public health concern. Therefore research and development of novel and safe anti-coccidial agent is practically significant. Plants are recognized as a wonderful source for human as well as animal medicines. *Bidens pilosa*, an Asteraceae family, is claimed as folk medicines for a variety of diseases.

SUMMARY OF THE INVENTION

In one aspect, the invention relates to a composition for prevention, inhibition and/or treatment of coccidiosis in an animal in need thereof. The composition comprises an effective amount of *Bidens pilosa*, an active constituent thereof, or an active compound isolated therefrom.

In another aspect, the invention relates to a composition for use in preventing and/or treating coccidiosis, and/or enhancing growth in an animal, the composition comprising an animal led and an effective amount of a compound comprising a polyacetylenic compound having a chemical structure of $$R_1 \!-\!\!\left(\!C\!\equiv\!C\!\right)_{\!m}\!\!\left(\!\!\begin{array}{c}C\!=\!C\\H\quad H\end{array}\!\!\right)_{\!n}\!\!\left(\!\!\phantom{x}\!\!\right)_{\!o}\!\overset{OR_2}{\underset{\phantom{x}}{\diagup}}\!\!\left(\!\!\phantom{x}\!\!\right)_{\!p}\!OR_3, \quad (I)$$

wherein.
  $R_1$ is H or CH3;
  $R_2$ is monosaccharide;
  $R_3$ is H or $COCH_2COOH$;
  m=3 or 4;
  n=0 or 1;
  o=1 or 2; and
  p=1 or 2.

Yet in another aspect, the invention relates to a composition comprising: (a) an animal feed; and (b) *Bidens pilosa*, an active constituent thereof, or an isolated compound comprising a polyacetylenic compound having a chemical structure of $$R_1 \!-\!\!\left(\!C\!\equiv\!C\!\right)_{\!m}\!\!\left(\!\!\begin{array}{c}C\!=\!C\\H\quad H\end{array}\!\!\right)_{\!n}\!\!\left(\!\!\phantom{x}\!\!\right)_{\!o}\!\overset{OR_2}{\underset{\phantom{x}}{\diagup}}\!\!\left(\!\!\phantom{x}\!\!\right)_{\!p}\!OR_3, \quad (I)$$

wherein
  $R_1$ is H or CH3;
  $R_2$ is monosaccharide;
  $R_3$ is H or $COCH_2COOH$;
  m=3 or 4;
  n=0 or 1;
  o=1 or 2; and
  p=1 or 2, in an effective amount for preventing and/or treating coccidiosis, and/or enhancing growth in an animal in need thereof.

This invention is based on the unexpected finding that a naturally occurring polyacetylenic compound was effective in preventing and/or treating coccidiosis, and/or promoting growth in an animal in need thereof.

The polyacetylenic compound may be a pure compound of formula (I):

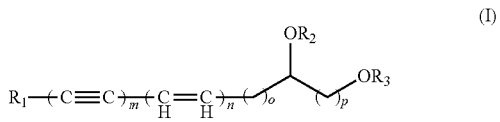

In this formula, $R_1$ is H, $C_1$-$C_{10}$ alkyl, $C_2$-$C_{10}$ alkynyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; $R_2$ is a monosaccharide residue; $R_3$ is H or $C_1$-$C_{10}$ alkyl; m is 2, 3, or 4; n is 0, 1, 2, or 3; o is 0, 1, 2, 3, or 4; and p is 1, 2, 3 or 4.

The term "pure compound" refers to a compound that has a purity of at least 80% (e.g., 95% or 99%). Referring to formula (I), a subset of the polyacetylenic compounds described above are those in which $R_1$ is $C_1$-$C_{10}$ alkyl (e.g., methyl) $R_2$ is glycopyranose; $R_3$ is H or $C_1$-$C_{10}$ alkyl; m is 4; n is 0; o is 2; and p is 1.

The term "alkyl" refers to a saturated, linear or branched, non-aromatic hydrocarbon moiety, such as $CH_3$, —$CH_2$—, or branched $(CH_3)_2CH_2$—. The term "alkenyl" refers to a linear or branched, non-aromatic hydrocarbon moiety having at least one double bond, such as $CH_2$=CH—, or —CH=CH—. The term "alkynyl" refers to a linear or branched, non-aromatic hydrocarbon moiety having a least one triple bond, such as CH≡C— or —C≡C—. The term "cycloalkyl" refers to a saturated non-aromatic cyclic hydrocarbon moiety, such as cyclohexyl. The term "cycloalkenyl" refers to a non-aromatic cyclic hydrocarbon moiety that contains at least one double bond in the ring, such as cyclohexenyl. The term "heterocycloalkyl" refers to a saturated non-aromatic, cyclic moiety having at least one ring heteroatom (e.g., O, N or S), such as 4-tetrahydropyranyl. The term "heterocycloalkenyl" refers to a non-aromatic, cyclic moiety having at least one ring heteroatom and at least one double bond in the ring, such as pyranyl. The term "aryl" refers to a hydrocarbon moiety having at least one aromatic ring. Examples of aryl moieties include phenyl, phenylene, biphenyl, naphthyl, naphthylene, pyrenyl, anthryl and phenanthryl. The term "heteroaryl" refers to a moiety having at least one aromatic ring which contains at least one heteroatom. Examples of heteroaryl moieties include furyl, furylene, fluorenyl, pyrrolyl, thienyl, oxazolyl, imidazolyl, thiazolyl, pyridyl, pyrimidinyl, quinazolinyl, isoquinolyl, and indolyl.

Alkyl, alkenyl, alkynyl, cycloalkyl, cycyclolalkyl, heterocycloalkyl, heterocycloalkenyl, aryl, and heteroaryl mentioned herein include both substituted and unsubstituted moieties. Examples of substituents on cycloalkyl, cycloalkenyl, heterocycloalkyl, heterocycloalkenyl, aryl, and heteroaryl include, but are not limited to $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, heteroarylamino, diheteroarylamino, $C_1$-$C_{10}$ alkylsulfony, arylsulfonyl, heteroarylsulfonyl, $C_1$-$C_{10}$ alkylsulfonamide, arylsulfonamide, heteroarylsulfonamide $C_1$-$C_{10}$ alkylimino, arylimino, $C_1$-$C_{10}$ alkylsulfonimino, arylsulfonimino, hydroxyl, halo, thio $C_1$-$C_{10}$ alkylthio, arylthio, aminothioacyl, amidino, guanidine, ureido, cyano, nitro, nitroso, azido, acyl, thioacyl, acyloxy, carboxyl, amido, carbamoyl, and carboxyl, and carboxylic ester. Examples of substituents on alkyl, alkenyl, and alkynyl include all of the above-recited substituents except $C_1$-$C_{10}$ alkyl. $C_2$-$C_{10}$ alkenyl, and $C_2$-$C_{10}$ alkynyl. Cycloalkyl, cycloalkenyl, heterocycloalkyl, heterocycloalkenyl, aryl, and heteroaryl can also be fused with each other.

A subset of the polyacetylenic compounds are those in which $R_1$ is $C_1$-$C_{10}$ alkyl (e.g., methyl); $R_2$ is a glucose, galactose, fucose, mannose, gulose residue, or H; $R_3$ is H; m is 4, n is 0, o is 2, and p is 1. A polyacetylenic compound may be administered to the subject as a pure compound in a pharmaceutical composition or as a component in a *Bidens pilosa* extract.

In a further aspect, this invention features a method for preventing and/or treating coccidiosis, and/or promoting growth in an animal in need thereof by administering to a subject in need an effective amount of a *Bidens pilosa* preparation. Such a preparation can be obtained by stirring pulverized *Bidens pilosa* plants in water at an elevated temperature (e.g., at 50° C. or 100° C.) to form a suspension, and collecting a supernatant of the suspension. The supernatant can be further extracted with an alcohol (e.g., n-butanol) to provide an enriched preparation. The *Bidens pilosa* preparation contains one or more of the polyacetylenic compounds of the just-mentioned formula (I). For example, it contains cytopiloyne:

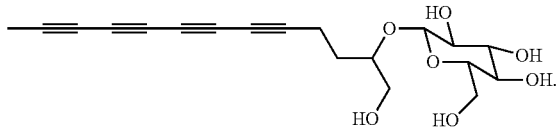 [SMILES: CC#CC#CC#CC#CCCC(CO)OC1OC(CO)C(O)C(O)C1O]

The polyacetylenic compounds described above include the compounds themselves, as well as their salts, prodrugs, and solvates, if applicable. Such salts, for example, can be formed by interaction between a negatively charged substituent (e.g., carboxylate) on a polyacetylenic compound and a cation. Suitable cations include, but are not limited to, sodium ion, potassium ion, magnesium ion, calcium ion, and an ammonium cation (e.g., tetramethylammonium ion). Likewise, a positively charged substituent (e.g., amino) on a polyacetylenic compound can form a salt with a negatively charged counterion. Suitable counterions include, but are not limited to, chloride, bromide, iodide, sulfate, nitrate, phosphate, or acetate. Examples of prodrugs include esters and other pharmaceutically acceptable derivatives, which, upon administration to a subject, are capable of providing above compounds described above. A solvate refers to a complex formed between a polyacetylenic compound and a pharmaceutically acceptable solvent. Examples of pharmaceutically acceptable solvents include water, ethanol, isopropanol, n-butanol, ethyl acetate, and acetic acid.

The polyacetylenic compounds may contain one or more asymmetric centers or a non-aromatic double bond. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a composition, including a *Bidens pilosa* extract, containing one or more of the polyacetylenic compounds described above for use in preventing and/or treating coccidiosis, and/or promoting growth in an animal in need thereof, and the use of such a composition for the manufacture of a medicament for the just-mentioned use.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 4. shows the effect of cytopiloyne on the sick bird appearance and clinical symptoms in the chickens. One-day-old chickens were fed with control diet for 14 days. On day 14, the birds were infected with vehicle (CTR) or E. tenella (ET) and fed with control diet (CTR and ET groups) and the diet containing 45 µg/kg cytopiloyne (ET+CP) for additional 7 days. The sick bird appearance (FIG. 4A), bloody stool (FIG. 4B) and cecal pathology in low magnification power (FIG. 4C) and (FIG. 4D) in high magnification power were measured.

FIG. 5 shows the effect of cytopiloyne on mucosal pathology in the chickens. Ceca of the same chickens from FIG. 4 were fixed with 10% formalin and embedded with parafin.

DETAILED DESCRIPTION OF THE INVENTION

Definitions

Figure 1A:
FIG. 1. shows preparation of B. pilosa powder and diet formulation. The photo of B. pilosa (A), air-dried B. pilosa (B) and sieved part of the grounded B. pilosa (C).

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. in the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Coccidian parasites infect the intestinal tracts of animals. Infection with these parasites is known as coccidiosis. Coccidiosis is a usually acute invasion and destruction of intestinal mucosa by protozoa of the genera Eimeria or Isospora. Infection is characterized by diarrhea, fever, inappetence, weight loss, emaciation, and sometimes death. Coccidiosis is a serious disease in cattle, sheep, goats, pigs, poultry, and also rabbits, in which the liver as well as the intestine can be affected. In dogs, cats. and horses, it is less often diagnosed but can result in clinical illness. Eimeria is a genus of Apicomplexan parasites that includes various species responsible for the poultry disease coccidiosis.

The term "constituent" or "constituents" used herein refers to biologically active phytochemicals present in Bidens pilosa that has anti-coccidiosis and/or growth enhancement effects. Plant constituents or active ingredients, are elements that have a marked, medical action upon the body.

An animal feed refers to food given to domestic livestock, and pet (companion animal) food.

The term "pure compound" used herein refers to a compound that has a purity of at least 80% (e.g., 95% or 99%).

The term "treating" or "treatment" refers to administration of an effective amount of Bidens pilosa or its phytochemicals (e.g., polyacetylenic compounds such as cytopiloyne) to a subject, who has coccidosis, or a symptom or predisposition toward such a disease, with the purpose to cure, alleviate, relieve, remedy, ameliorate, or prevent coccidosis, the symptoms of it, or the predispositions towards it.

As used herein, "effective amount" or "sufficient amount" of Bidens pilosa or a compound refers to an amount that may be therapeutically effective to enhance growth, and/or inhibit, prevent, or treat a symptom of a particular disease, disorder, condition, or side effect described herein. For example, "an effective amount" may refer to the amount that is required to confer a therapeutic or a desired effect on the treated subject. Effective doses will vary, as recognized by those skilled in the art, depending on route of administration, excipient usage, and the possibility of co-usage with other therapeutic treatment.

The invention relates to the discovery of novel and safe anti-coccidial compounds from the nature. The invention relates to the discovery of the effects of *B. pilosa* on the growth and *Eimeria* infection in poultry such as chickens.

*B. pilosa* powder was prepared first. Then chicken diets were formulated by mixing with different percentages of *B. pilosa* powder. The advantage of *B. pilosa* on growth performance in chickens was tested. It was found that 10% or less of BPP enhanced growth and feed conversion in chickens. The therapeutic effect of *B. pilosa* on coccidiosis in chickens was evaluated by survival rate, excreted oocysts and gut lesions of the chickens. It was discovered that BPP effectively reduced mortality, clinical symptoms and excreted oocysts following the *Eimeria* challenge. Overall, *B. pilosa* was demonstrated to be beneficial for chicken growth and therapeutically effective against coccidiosis in chickens. The data also suggest the potential of *B. pilosa* to treat *Eimeria* infection.

Polyacetylenic Compounds

Polyacetylenic compounds (e.g., cytopiloyne) can be isolated from *Bidens pilosa*. Whole *Bidens pilosa* plants are first pulverized and then stirred in heated water. After removal of insoluble materials (e.g., by filtration, decantation, or centrifugation), the resultant supernatant is subjected to liquid chromatography (e.g., high-pressure liquid chromatography) or other suitable methods to afford pure polyacetylenic compounds. The pure compounds thus obtained can be further derivatized to provide a number of other polyacetylenic compounds of this invention (U.S. Pat. No. 7,763,285, and Kusano et al (JP 2004083463), all of which are incorporated herein by reference in their entireties).

The polyacetylenic compounds described above can also be prepared by conventional methods. Below are three reaction schemes illustrating, synthetic routes to a polyacetylenic compound of this invention.

Butane-1,24-triol (i) is reacted with acetone to form a protected 1,2,4-triol compound (ii), which can be readily transformed to an iodo derivative (iii). Compound (iii) is then reacted with ethynyltrimethylsilane, under a basic condition (e.g., n-BuLi), to give (4-(2,2-dimethyl-1,3-dioxolan-4-yl) but-1-ynyl)trimethylsilane (iv). Compound (iv) is subsequently treated with an acid (e.g., acetic acid), followed by a coupling reaction with 2-bromoglucopyranose to afford an adduct (v). Compound (v) can be further treated with potassium fluoride to afford 2-phenyl-4H-chromen-4-one (vi).

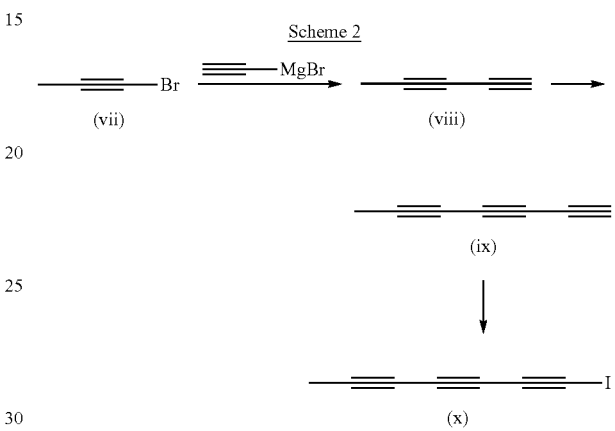

Scheme 2

1-Bromoprop-1-yne (vii) is reacted with ethynylmagnesium bromide to afford penta-1,3-diyne (viii), which is further converted to hepta-1,3,5-triyne (ix). Compound (ix) can be readily transformed to 1-iodohepta-1,3,5-triyne (x) under a basic condition (e.g., n-BuLi), followed by addition of are iodo compound (e.g., $I_2$).

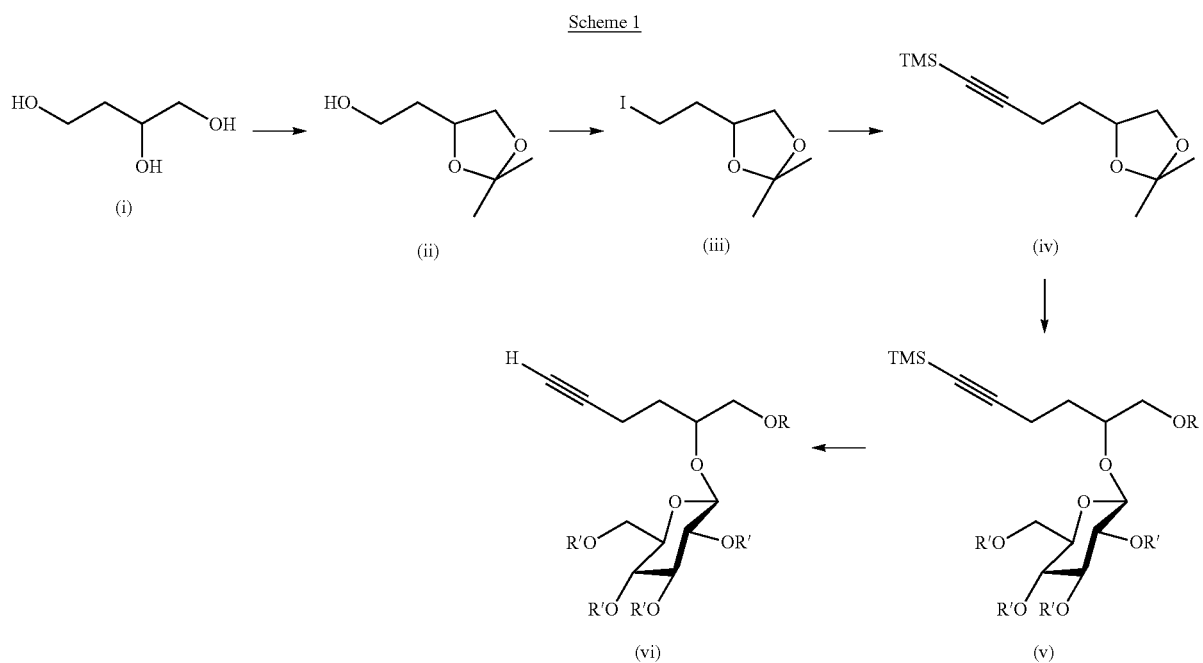

Scheme 1

Scheme 3

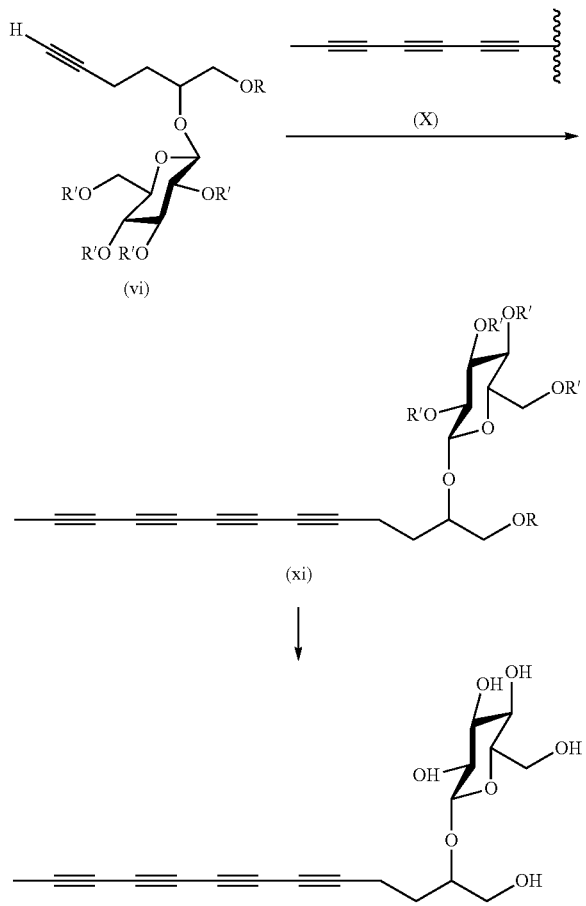

Scheme 3 demonstrates a coupling reaction between an acetylene derivative (vi), obtained from Scheme 1, and 1-iodohepta-1,3,5-triyne (x), obtained from Scheme 2, to a tetrayne compound (xi). Removal of protecting groups affords a polyacetylenic compound, 2β-D-glucopyranosyloxy-1-hydroxytrideca-5,7,9,11-tetrayne, a compound of this invention.

Synthetic chemistry transformations useful in synthesizing applicable compounds are described, for example, in R. Larock, *Comprehensive Organic Transbpiunions*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

This invention features a method of administrating an effective amount of one of the above-described polyacetylenic compounds or a *Bidens pilosa* preparation containing such a compound to a subject in need thereof.

A composition for oral administration can be any orally acceptable dosage form including capsules, tablets, emulsions, and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

*Bidens pilosa* plants were collected from the campus of Academia Sinica, Taiwan. Approximately 10 kg of cleaned and crushed plants, in their entirety, was refluxed in 40 L of water for two hours. After removal of aqueous phase, insoluble materials was again refluxed in 25 L of water for two hours. The combined aqueous solutions (approximately 65 L were evaporated in vacuo to yield a residue, which was subsequently suspended in 1.0 L of water and extracted with 1.0 L of n-butanol for three times. The n-butanol fraction was first evaporated on a vacuum rotary evaporator under reduced pressure and then lyophilized to provide a crude product of cytopiloyne (37.7 g).

The crude product was subsequently chromatographed over a RP-18 silica gel column with a CH$_3$OH/H$_2$O gradient solvent system to give sub-fractions BPB1, BPB2, BPB3, and BPB4. The BPB3 fraction, eluted by 70% CH$_3$OH, was further fractionated by semi-preparative HPLC using a CH$_3$OH/H$_2$O solvent system. Cytopiloyne was obtained and characterized by $^1$H NMR and $^{13}$C NMR.

$^1$H NMR (500 MHz, CDOD$_3$) δ 1.78 (2H, q, J=6.8 Hz), 1.98 (3H, s), 2.58 (2H, t, J=6.8 Hz), 3.19 (1H, dd, J=9.1, 7.8 Hz), 3.30 (1H, m), 3.34 (1H, m), 3.59 (2H, m) 3.65 (1H, dd, J=12.0, 6.5 Hz), 3.75 (1H, p, J=6.8 Hz), 3.85 (1H, dd, J=12.0, 1.7 Hz), 4.32 (1H, d, J=7.8 Hz); $^{13}$C NMR (125 MHz, CDOD$_3$) δ 3.8, 16.1, 31.4, 60.0, 60.9, 61.8, 62.4, 62.6, 64.9, 65.8, 66.2, 71.5, 75.2, 77.9, 81.6, 104.8.

In one aspect, the invention relates to a composition for use in prevention, inhibition and/or treatment of coccidiosis in an animal in need thereof, the composition comprising an effective amount of *Bidens pilosa*, an active constituent thereof, or an active compound isolated therefrom.

In another aspect, the invention relates to a composition for use in preventing and/or treating coccidiosis, and/or enhancing growth in an animal in need thereof, the composition comprising an animal feed and an effective amount of a compound comprising a polyacetylenic compound having a chemical structure of

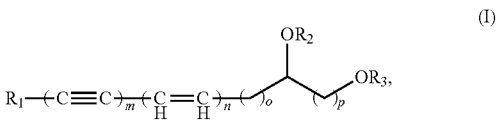

(I)

wherein
R$_1$ is H or CH$_3$;
R$_2$ is monosaccharide;
R$_3$ is H or COCH$_2$COOH;
m=3 or 4;
n=0 or 1;
o=1 or 2; and
p=1 or 2.

The composition may be prepared by adding the *Bidens pilosa*, the active constituent thereof, or the active compound isolated therefrom into an animal feed prior to the use. The composition may be in a dosage form selected from the group consisting of an oral dosage form, a capsule dosage form, a suppository dosage form and a parenteral dosage form. The composition may further comprise an animal feed such as a chicken feed.

In another embodiment of the invention, the composition comprises the animal feed and 0.0005%~15% (w/w) of *Bidens pilosa* (e.g., *Biden pilosa* powder).

In another embodiment of the invention, the *Biden pilosa* may be in a form of powder.

In another embodiment of the invention, the active constituent or the active compound isolated therefrom comprises a polyacetylenic compound having a chemical structure of

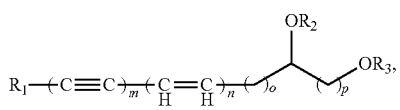

wherein
R$_1$ is H or CH$_3$;
R$_2$ is monosaccharide;
R$_3$ is H or COCH$_2$COOH;
m=3 or 4;
n=0 or 1;
o=1 or 2; and
p=1 or 2.

The polyacetylenic compound may be selected from the group consisting of

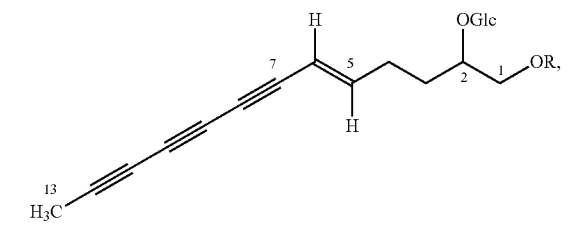

A: R = COCH$_2$COOH
A': R = H

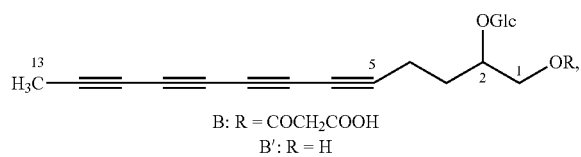

B: R = COCH$_2$COOH
B': R = H and

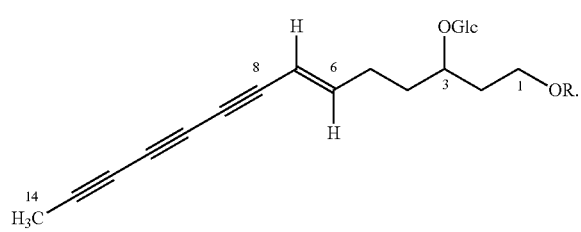

C: R = COCH$_2$COOH
C': R = H

In another embodiment of the invention, the animal is administered the polyacetylenic compound at a dose of no less than 45 μg/kg body weight. The animal may be a non-human animal. The animal may be selected from the group consisting of fish, birds, reptiles, and non-human mammals.

Yet in another aspect, the invention relates to a composition comprising: (a) an animal feed; and (b) *Bidens pilosa*, an active constituent thereof, or an isolated compound comprising a polyacetylenic compound having a chemical structure of

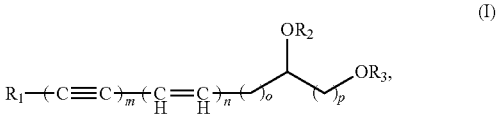

wherein
R$_1$ is H or CH$_3$;
R$_2$ is monosaccharide;
R$_3$ is H or COCH$_2$COOH;
m=3 or 4;
n=0 or 1;
o=1 or 2; and
p=1 or 2, in an effective amount for preventing and/or treating coccidiosis, and/or enhancing growth in an animal in need thereof.

In one embodiment of the invention, the animal feed is selected from the group consisting of poultry feed, fish food, reptile food, bird feed, and non-human mammal food. For example, the animal feed may be a chicken feed. The compound may be isolated from the *Bidens pilosa*.

In another embodiment of the invention, the composition comprises the animal feed and cytopiloyne at the ratio of 0.01 mg~3 g of cytopiloyne per kilogram of the animal feed. The composition may comprise the animal feed and no more than 15% (w/w) of *Bidens pilosa* and/or no less than 0.0005% (w/w) of *Bidens pilosa*.

In another aspect, the invention relates to a composition for preventing and/or treating coccidiosis, and/or promoting, growth in a non-human animal in need thereof, the composition comprising an animal feed and an effective amount of *Bidens pilosa* and/or an active compound isolated therefrom.

The animal may be a non-human animal such as a chicken. The composition is also for use in causing an increase in the body weight and feed conversion in the chicken. The coccidiosis comprises *Eimeria* infection.

In another embodiment of the invention, the active compound comprises a chemical structure of

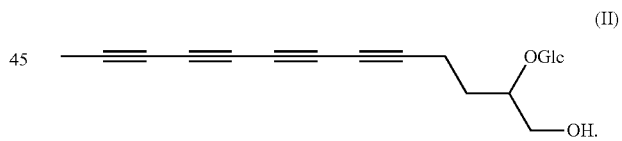

In another embodiment of the invention, the composition comprises the animal feed and no more than 15% (w/w), or no more than 10% (w/w) of *Bidens pilosa*, and/or no less than 0.0005% (w/w) of *Bidens pilosa*. The composition may comprise the animal feed and *Bidens pilosa* in the range of 0.0005%~15% (w/w), or 0.0005%~10% (w/w), or 0.0005%~5% (w/w), or 0.0005%~1% (w/w), or in the range of 0.5%~5% (w/w), or 0.5%~1% (w/w), or no more than 1% (w/w).

The animal may be administered *Bidens pilosa* at a dose ranging from 0.5 mg to 15,000 mg/kg of body weight.

The *Bidens pilosa* may be in a form of powder. Calculation of the percentage of *Bidens pilosa* powder (BPP) is as follows: *Biden pilosa* powder weight/*Biden pilosa* powder weight+basic chicken feed=% of BPP.

By 0.0005%~15% (w/w) it meant that all ten-thousandth, thousandth, hundredth tenth and integer unit amounts within the range are specifically disclosed as part of the invention.

Thus, 0.0001%, 0.0002%, 0.0003% ... 0.001%, 0.002%, 0.003% ... 0.01%, 0.02%, 0.03% ... 0.1%, 0.2%, 0.3%, 0.4%, 0.5%, 0.6%, 0.7%, 0.8%, 0.9% and 1%, 2%, 3%, 4% ... 13%, 14%, and 15% unit amounts are included as embodiments of this invention.

In another embodiment. of the invention, the composition comprises an animal feed and cytopiloyne, wherein the ratio of cytopiloyne to the animal feed is 0.01 mg~3 g of cytopiloyne per kilogram of the animal feed. The animal may be administered 0.001 mg~3 mg of cytopiloyne per kilogram body weight. By 0.01 mg~3 g it meant that all hundredth, tenth and integer unit amounts within the range are specifically disclosed as part of the invention. Thus, 0.01 mg, 0.02 mg, 0.03 mg ... 0.1 mg 0.2 mg, 0.3 mg ... 0.998 g 0.999 g, 1 g ... 1.98 g, 1.99 g, 2 g ... 2.8 g, 2.9 g and 3 g unit amounts are included as embodiments of this invention.

The animal may comprise a chicken having *Eimeria* infection. The aforementioned composition may also be used for causing a reduction in mortality, clinical symptoms and excreted oocysts in the chicken. The aforementioned compound may comprise cytopiloyne.

Further in another aspect, the invention relates to a composition comprising: a) an animal feed; and b) *Bidens pilosa* or an isolated compound comprising a chemical structure of

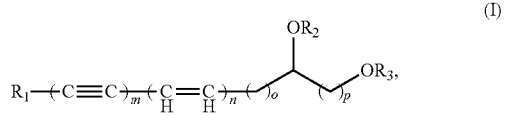

(I)

wherein
  $R_1$ is H or CH3;
  $R_2$ is monosaccharide;
  $R_3$ is H or $COCH_2COOH$;
  m=3 or 4;
  n=0 or 1;
  o=1 or 2; and
  p=1 or 2,
in an effective amount for preventing and/or treating coccidiosis, and/or enhancing growth in an animal in need thereof.

The isolated compound may be chemically synthesized or isolated from *Bidens pilosa*. In one embodiment of the invention, the isolated compound comprises a chemical structure of

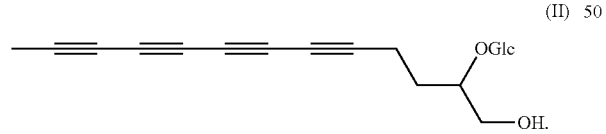

(II)

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Materials and Methods

Chemicals
Maduramicin, PBS, hematoxylin and eosin Y were purchased from Sigma-Aldrich (St Louis, Mo., USA). *B. pilosa* L, was shade dried and ground into powder. The powder was mixed with chicken diet as indicated. To evaluate the quality control of each batch of *B. pilosa* powder. HPLC was performed.

Birds, Diets, and Experimental Design
One-d-old Lohmann broiler chicks hatched. at Taichung Hatchery (Taiwan) were wing-banded upon arrival, weighed, and randomly placed in Petersime starter brooder units. At 1 and 2 d post-hatch, the birds were given free access to water and diets. The diets were formulated by mixing the base diet (Chicken feed, Taiwan Sugar Corporation) with carrier alone (control diet) or the indicated dose of *B. pilosa* power (BPP diet). In case of cytopiloyne experiments, the animal was administered with 45 μg of isolated cytopiloyne each day. After grouping, birds were tube-fed with *Eimeria* oocysts. Growth performance (body weight and feed conversion), pathology (bloody droppings and gut morphometry) and survival rate were measured and examined. All birds were maintained in the institutional animal facility and handled according to the guidelines of the Academia Sinica Institutional Animal Care and Utilization Committee.

Immunohistochemical Staining
Multiple parallel sections of the pancreata from chickens that had access to control diet and BPP diet for 14 days were flash-frozen. The sections were stained with hematoxylin and eosin or anti-insulin antibody, with development of diaminobenzidine tetrahydrochloride, followed by image analysis, Chang et al (2007) "Cytopiloyne, a polyacetylenic glucoside, prevents type 1 diabetes in nonobese diabetic mice" *J Immunol* 178(11): 6984-6993, which is herein incorporated by reference in its entirety.

Statistical Analysis
The results from three or more independent experiments were presented as mean±S.E. Data were analyzed by ANOVA. Differences of P value less than 0.05 were considered statistically significant.

Figure 1B:
Figure 1C:
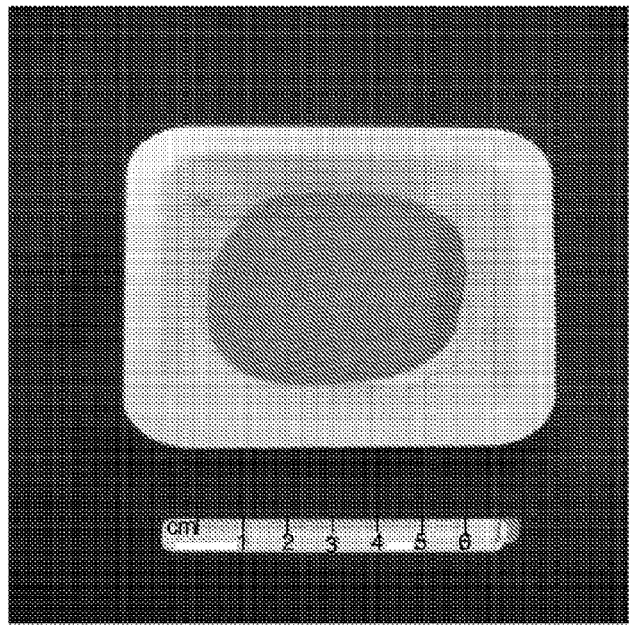

Results
Preparation of *B. pilosa* Powder and Formulation of the Chicken Diet with *B. pilosa* Powder.
To prepare *B. pilosa* powder, whole plant of *B. pilosa* was harvested and washed. The plant was shade-dried for 3 days and grounded into powder (FIG. 1). The *B. pilosa* powder (BPP) was sieved with mesh and used as the material for the formulation. BPP diet was formulated by mixing the normal chicken diet (control diet) with the indicated amount of BPP (5%, 10%, 15% and 20% of total weight (the amount of normal diet and BPP).

Figure 2A:
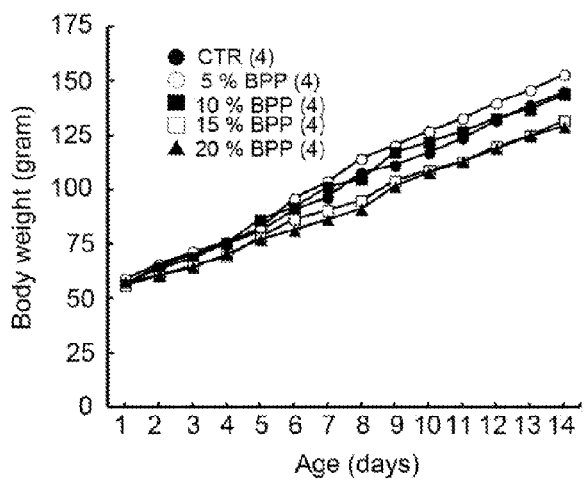
FIG. 2. shows the effect of BPP on growth and feed conversion in the chickens. (A) One-d-old chickens had free access to water and feed (control diet, 5%, 10%, 15% and 20% BPP diet). (A) The body weight of the birds and consumption of different diets were measured. (B) Food conversion ratio is obtained by the ratio of weight gain to the consumed diet. The number of the birds is indicated in the parentheses.
FIGS. 2C-D show the appearances and feces of chickens led with the different BPP levels feed, in which the left side was control and right side was 5% BPP supplement in feed FIG. 3. shows the effect of BPP on the survival rate (FIG. 3A), sick bird appearance (FIG. 3B) and clinical symptoms (FIG. 3C) in the chickens. One-day-old chickens were fed with control diet for 14 days. On day 14, the birds were infected with vehicle (CTR) or E. tenella (ET) and fed with control diet (CTR and ET groups) and the diet containing 6 mg/kg maduramicin (ET+Mad), or 5%, or 1 or 0.5% of BPP (ET+BPP) for additional 7 days. After the birds were sacrificed, the cecum was dissected and fixed for hematoxylin and eosin Y staining. The representative images of cecal hemorrhagic lesions (FIG. 3D) and histopathology (FIG. 3E) are shown.
Figure 2B:
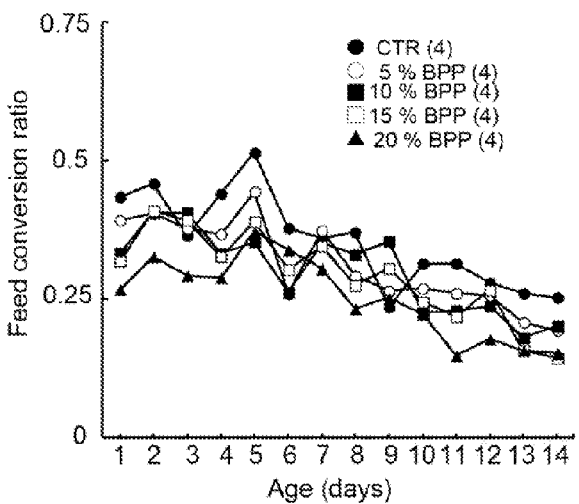
Figure 2C:
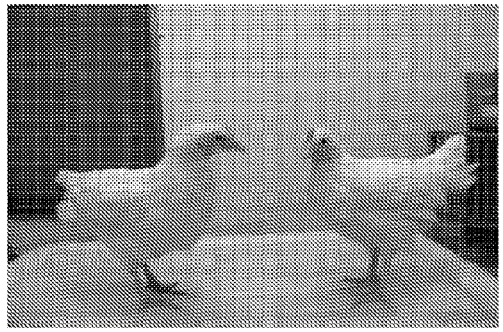
Figure 2D:

Effect of BPP on Growth Performance and Feed Conversion
To evaluate the effect of BPP diet on the growth and feed conversion in chicks, the 1-day-old birds had daily free access to control diet or BPP diet for 14 days. The body weight and feed consumption were measured. The birds given 5% BPP diet grew slightly better than those given the normal diet. The birds given 10% BPP diet grew as well as those given the normal diet. The birds given 15% BPP diet and 20% BPP diet grew slightly worse than those given the normal diet (FIG. 2A). Unexpectedly, the feed conversion of BPP diets was better than control diet (FIG. 2B).

Effect of BPP on Blood Leukocytes

To evaluate the effect of BPP diet on the leukocytes, the 1-day-old birds had daily free access to control diet or BPP diet for 14 days. The leukocyte composition was measured. We found that 5% BPP diet did not affect the composition of leukocytes in blood of the birds (Table 1). Table 1 shows the composition of the leukocytes in blood of the birds. One-d-old chickens were given control diet (CTR) and the diet containing 5% BPP (5% BPP) for 14 days. The blood of the birds was collected for analysis. The number of the birds in each group is indicated in the parentheses.

TABLE 1

|  | Monocyte | Eosinophils | Basophils | Lymphocytes | Heterophils |
| --- | --- | --- | --- | --- | --- |
| CTR (4) | 4.7 ± 1.2% | 24.3 ± 0.6% | 2.3 ± 0.6% | 55.7 ± 2.1% | 33.0 ± 2.6% |
| 5% BPP (4) | 6.3 ± 0.6% | 5.7 ± 2.9% | 2.0 ± 0.0% | 55.0 ± 3.0% | 30.7 ± 1.5% |

Effect of BPP on Survival Rate and Clinical of the Chickens Following *Eimeria* Infection.

Figure 3A:
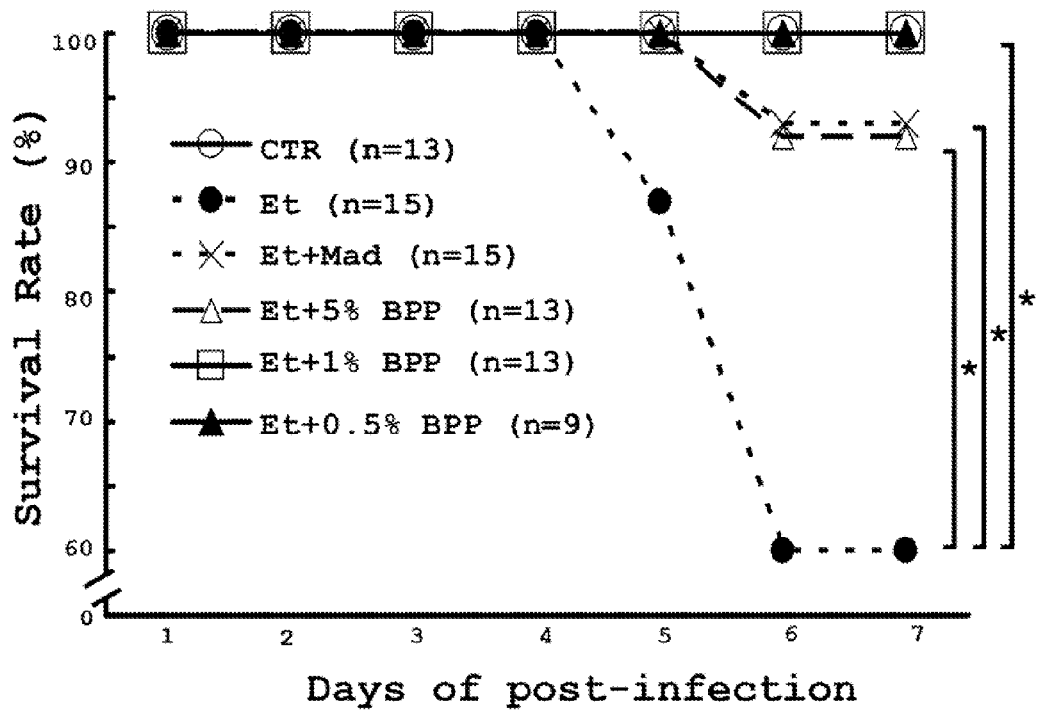

Since *B. pilosa* was claimed to treat protozoan and bacterial infections, we tested whether *B. pilosa* could protect the chickens from coccidiosis. To this end, we infected the 7-d-old birds with vehicle and *Eimeria* occysts. The birds were given control diet, the control diet mixed with maduramicin, a commercial anti-coccidial, and 10% BPP diet. We found that as expected, the birds without *Eimeria* infection survived 100% 7 days post-infection. In contrast, 60% of the birds with *Eimeria* infection survived 7 days post-infection (FIG. 3A). However, treatment with a dose (6 mg/kg) of maduramicin and a dose (50 g/kg) of 10% BPP increased the survival rate of the birds with *Eimeria* infection by 30% (FIG. 3A). The body weight of each group of birds was shown in Table 2. We showed that *Eimeria* infection reduced body weight from 171.1 g to 132.5 g 21 days post-infection. However, treatment with maduramicin and BPP increased body weight from 132.5 g to 145.4 g and 154.3 g, respectively (Table 2). Overall, the data demonstrate that like maduramicin, BPP is therapeutically effective against *Eimeria* in chickens. Table 2 shows body weight of the birds with or without *Eimeria* infection. One-d-old chickens were fed with control diet for 14 days. On day 14, the birds were infected with vehicle (CTR) or *E. tenella* (ET) and fed with control diet (CTR and ET groups) and the diet containing 6 mg/kg maduramicin (ET+Mad) or 50 g/kg BPP (ET+BPP) for additional 7 days. Body weight was measured. The number of the birds in each group is indicated in the parentheses.

Figure 3B:
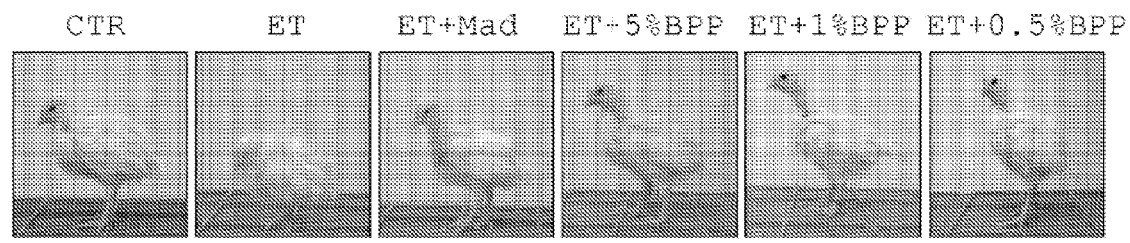
Figure 3C:
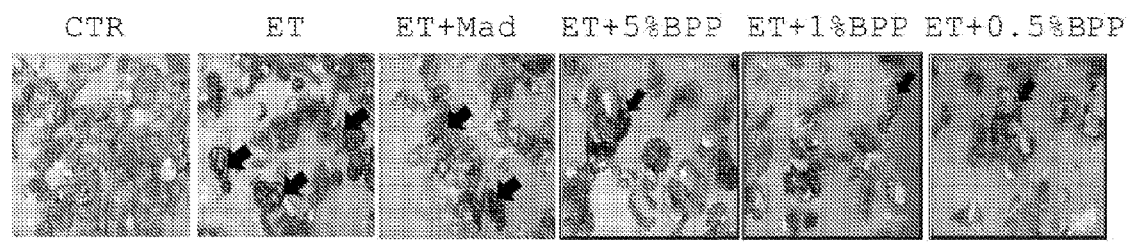

Next, we checked clinical symptoms of the chickens with or without *Eimeria* infection. The birds without *Eimeria* infection did not show the "sick bird appearance" such as droopiness, listlessness, and ruffled feather (FIG. 3B). In contrast, the birds with *Eimeria* infection show the typical "sick bird appearance" (FIG. 3B), Similarly, the birds, which were given the diet mixed with maduramicin and BPP, had no obvious sick bird appearance (FIG. 3B). Bloody droppings and diarrhea were observed in the birds infected with *Eimeria* (FIG. 3C). In contrast, treatment with maduramicin or BPP reduced bloody droppings and diarrhea (FIG. 3C).

TABLE 2

| Group | Day 0 | Day 7 | Day 14 | Day 21 |
| --- | --- | --- | --- | --- |
| CTR (2) | 38.5 ± 1.9 | 63.1 ± 1.4 | 111.5 ± 13.1 | 171.1 ± 0.8 |
| ET (2) | 34.5 ± 1.7 | 62.9 ± 3.5 | 103.5 ± 5.4 | 132.5 ± 2.9 |
| ET + Mad (4) | 36.3 ± 1.7 | 65.5 ± 5.7 | 111.8 ± 2.9 | 145.4 ± 6.2 |
| ET + BPP (4) | 37.0 ± 1.4 | 68.8 ± 2.1 | 111.5 ± 3.0 | 154.3 ± 3.9 |

Figure 3D:
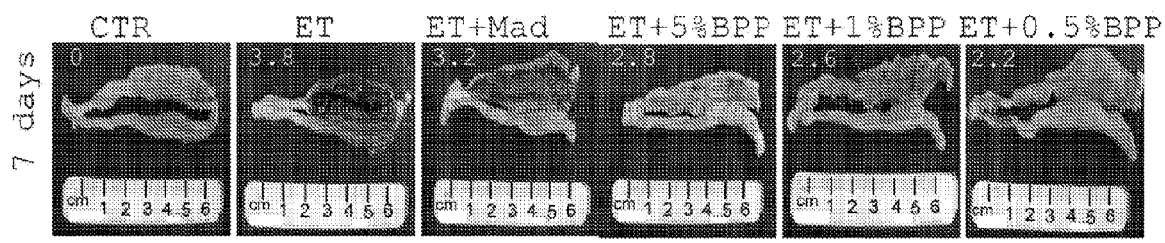
Figure 3E:
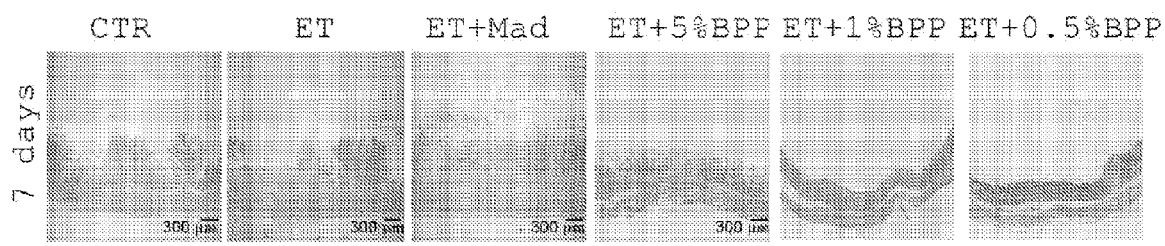
Figure 5A:
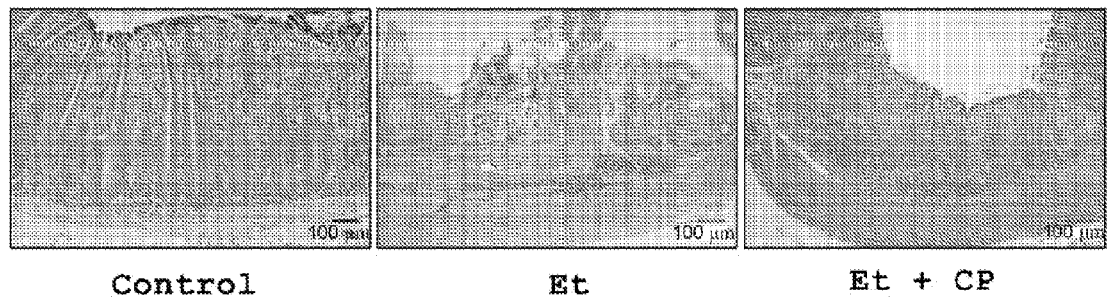
(FIG. 5A). The sections were stained with hematoxylin and eosin Y.
Figure 5B:
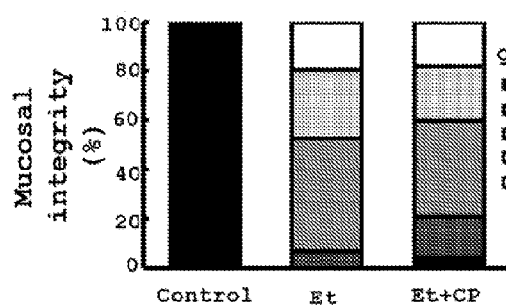
(FIGS. 5B-C). The images of cecal slides were photographed and mucosal severity (FIG. 5B) and inflammation (FIG. 5C) were determined.
Figure 5C:
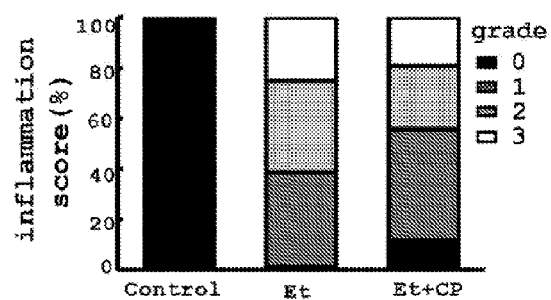
Figure 5D:
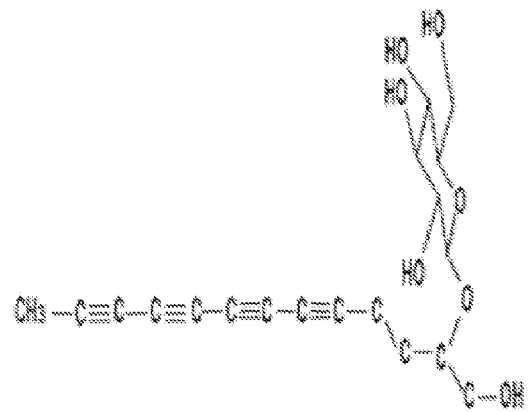
FIG. 5D shows the chemical structure of cytopiloyne.

The gut lesions of the birds 7 days post-infection were also examined. Hemorrhagic lesions in the cecum of the birds infected with *Eimeria* oocysts were observed (FIG. 3D). In contrast, treatment with maduramicin and BPP alleviated the severity of hemorrhagic lesions (FIG. 3D). Consistently, histostaining data revealed that the number of villi and the depth of crypts in the gut of the birds were reduced by *Eimeria* infection (FIG. 3E). Gut inflammation was observed in the birds with *Eimeria* infection (FIG. 3E). In contrast, like maduramicin treatment, BPP treatment increased the number of villi and the depth of crypts in the gut of the birds infected with *Eimeria* (FIG. 3E). Of note, BPP reduced gut inflammation to a greater extent than maduramicin (FIG. 3E).

The excretion of oocysts is an important indicator of the efficacy of anti-coccidial drug. Thus, we assessed the number of excreted oocysts from the chickens with *Eimeria* infection. We found that treatment with maduramicin and BPP reduced half the number of the excreted oocysts in the infected birds (Table 3). The data on the effect of BPP on the reduction of the excreted oocysts are consistent with the alleviation of the clinical symptoms by BPP. Table 3 shows the excretion of Oocysts in the feces of the birds with or without *Eimeria* infection. One-d-old chickens were fed with control diet for 14 days. On day 14, the birds were infected with vehicle (CTR) or *E. tenella* (ET) and fed with control diet (CTR and ET groups) and the diet containing 6 mg/kg maduramicin (ET+Mad) or 50 g/kg BPP (ET+BPP) for additional 7 days. The number of the excreted oocysts in the feces (oocysts per gram) of the birds was determined. The number of the birds in each group is indicated in the parentheses.

In summary, it has been demonstrated that certain portion of BPP in feed is beneficial for the growth of chickens. More importantly, BPP can prevent and treat coccidiosis in chickens as evidenced by the survival rate, sick bird appearance and clinical signs such as bloody droppings, diarrhea and gut lesions.

TABLE 3

| Group | Day 4 | Day 5 | Day 6 | Day 7 |
| --- | --- | --- | --- | --- |
| CTR (3) | 0 | 0 | 0 | 0 |
| ET (3) | 11 ± 1.0 | 169 ± 23.5 | 405 ± 70.1 | 503 ± 118.9 |
| ET + Mad (3) | 5 ± 0.3 | 78 ± 3.8 | 187 ± 4.7 | 343 ± 52.2 |
| ET + BPP (3) | 4 ± 0.5 | 84 ± 2.1 | 202 ± 10.4 | 363 ± 13.5 |

Example 2

FIG. 4. shows the effect of cytopiloyne on the sick bird appearance and clinical symptoms in the chickens. One-day-old chickens were fed with control diet for 14 days. On day 14, the birds were infected with vehicle (CTR) or *E. tenella* (ET) and fed with control diet (CTR and ET groups) and the diet containing 45 μg/kg cytopiloyne (ET+CP) for additional 7 days. The sick bird appearance (FIG. 4A), blood stool (FIG. 4B) and cecal pathology in low magnification power (FIG. 4C) and (FIG. 4D) in high magnification power were measured.

FIG. 5 shows the Effect of cytopiloyne on mucosal pathology in the chickens. Ceca of the same chickens from FIG. 4 were fixed with 10% formalin and embedded with parafin. (FIG. 5A). The sections were stained with hematoxylin and eosin Y. (FIGS. 5B-C). The images of cecal slides were photographed and mucosal severity (FIG. 5B) and inflammation (FIG. 5C) were determined. FIG. 5D shows the chemical structure of cytopiloyne.

Example 3

For prevention, inhibition and/or treatment of coccidiosis, animals are administered a composition comprising an effective amount of *Bidens pilosa*, an active constituent thereof, or an active compound isolated therefrom, *Bidens pilosa*, an active constituent thereof, or an active compound isolated therefrom may be added to the animal feed. The active constituent or active compound of *Bidens pilosa* may be extracted from the plant *Bidens pilosa*.

*Bidens pilosa* powder, an active constituent thereof, or an active compound isolated therefrom may be prepared in a form of a capsule. The composition may be prepared in a suppository dosage form. A pharmaceutically acceptable carrier may be added for preparing suitable dosage forms.

*Bidens pilosa* comprises at least the following polyacetylenic compounds A, A', B, B', C and C':

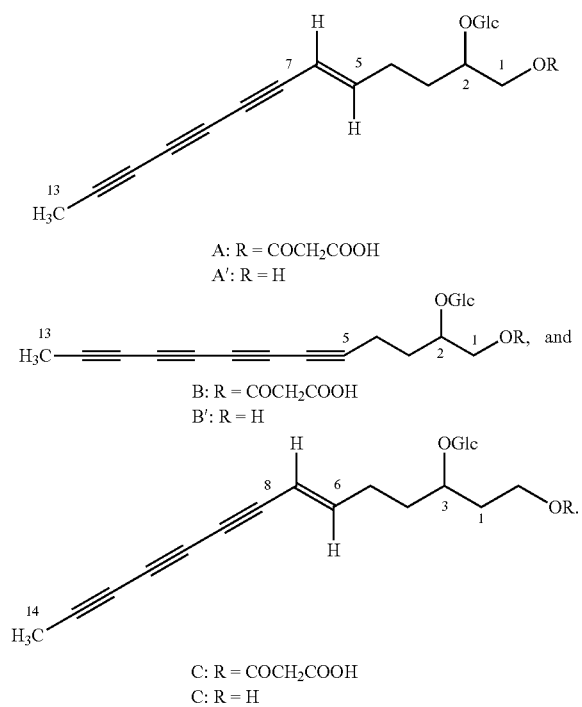

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Furthermore, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for alleviating or treating coccidiosis in an animal in need thereof comprising administering to the animal in need thereof a composition comprising:
   (a) an animal feed; and
   (b) a therapeutically effective amount of a *Bidens pilosa* extract or an active compound isolated from the *Bidens pilosa* extract to alleviate or treat the coccidiosis in the animal in need thereof, wherein the active compound isolated from the *Bidens pilosa* extract is a polyacetylenic compound of formula (I):

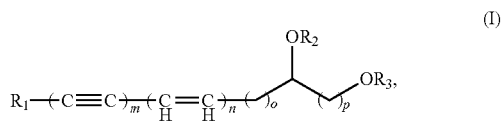

wherein
   $R_1$ is H or $CH_3$;
   $R_2$ is monosaccharide;
   $R_3$ is H or $COCH_2COOH$,
   m=3 or 4;
   n=0 or 1;
   o=1 or 2; and
   p=1 or 2.

2. The method of claim 1, wherein the composition is in a dosage form selected from the group consisting of oral, capsule, suppository and parenteral.

3. The method of claim 1, wherein the active compound is selected from the group consisting of:

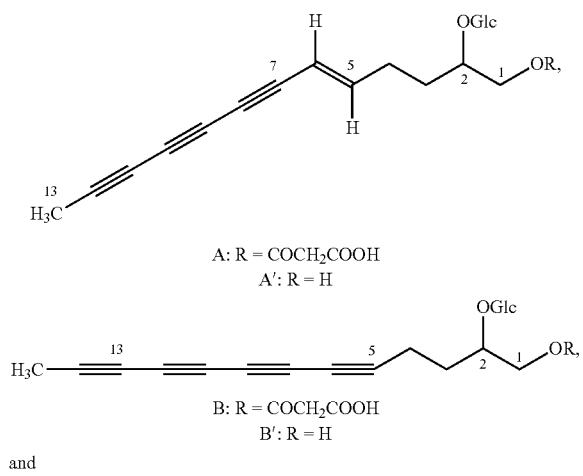

and

-continued

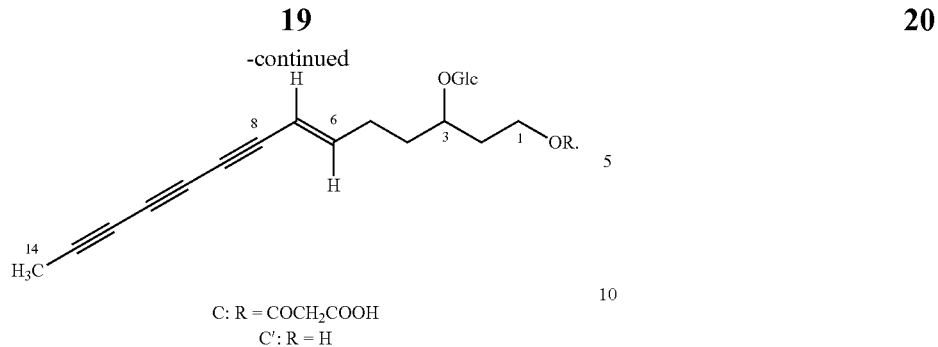

C: R = COCH$_2$COOH
C': R = H

4. The method of claim 1, wherein the animal in need thereof is administered the active compound isolated from the *Bidens pilosa* extract at a dose of no less than 1 μg/kg body weight of the animal in need thereof.

5. The method of claim 1, wherein the *Bidens pilosa* extract is in a form of a powder.

6. The method of claim 1, wherein the animal feed is a chicken feed.

7. The method of claim 1, wherein the animal is selected from the group consisting of fish, birds, and reptiles.

8. The method of claim 1, wherein the *Bidens pilosa* extract or the active compound isolated from the *Biden pilosa* extract is mixed into the animal feed.

* * * * *